(12) United States Patent
Luo

(10) Patent No.: US 11,840,537 B2
(45) Date of Patent: Dec. 12, 2023

(54) PREPARATION AND APPLICATION OF A 5-BROMOQUINAZOLINE DERIVATIVE

(71) Applicant: Mei Luo, Anhui (CN)

(72) Inventor: Mei Luo, Anhui (CN)

(73) Assignee: Hefei University of Technology, Anhui (CN)

( * ) Notice: Subject to any disclaimer, the term of this patent is extended or adjusted under 35 U.S.C. 154(b) by 0 days.

(21) Appl. No.: 17/488,317

(22) Filed: Sep. 29, 2021

(65) Prior Publication Data

US 2022/0135578 A1 May 5, 2022

(30) Foreign Application Priority Data

Nov. 3, 2020 (CN) .......................... 202011212029.8

(51) Int. Cl.
C07D 487/10 (2006.01)
C07B 41/04 (2006.01)

(52) U.S. Cl.
CPC ............ *C07D 487/10* (2013.01); *C07B 41/04* (2013.01); *C07B 2200/13* (2013.01)

(58) Field of Classification Search
CPC ................................... C07D 487/10
See application file for complete search history.

*Primary Examiner* — Susanna Moore

(57) ABSTRACT

A 5-bromoquinazoline derivative (I), structural formula thereof is as follows:

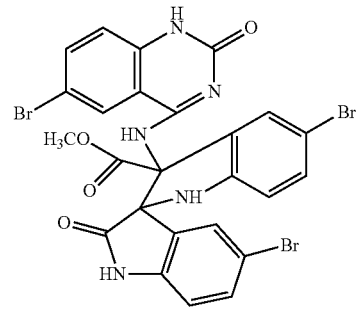

the synthesis method thereof comprises weighing 1.18 g of 5-bromoisatin, 2.5503 g of ammonium formate and 100 ml of absolute methanol in a 250 mL round-bottom flask, heating, stirring and refluxing for 48 h, stopping reaction, rotating to obtain 1.6033 g of filter residue crude product, carrying out column chromatography separation by using dichloromethane and absolute methanol according to a volume ratio of 1:1, and obtaining a target crystal compound I; the application of the 5-bromoquinazoline derivative compound crystal (I), as a catalyst has a good catalytic effect in nitrile silicification reaction of benzaldehyde and auto-polymerization reaction of benzophenone hydrazone, the conversion rates thereof respectively reach 39% and 76%, and the crystal (I) can be used as an anti-cancer reagent which has certain anti-cancer activity of breast cancer, liver cancer and lung cancer.

5 Claims, 1 Drawing Sheet

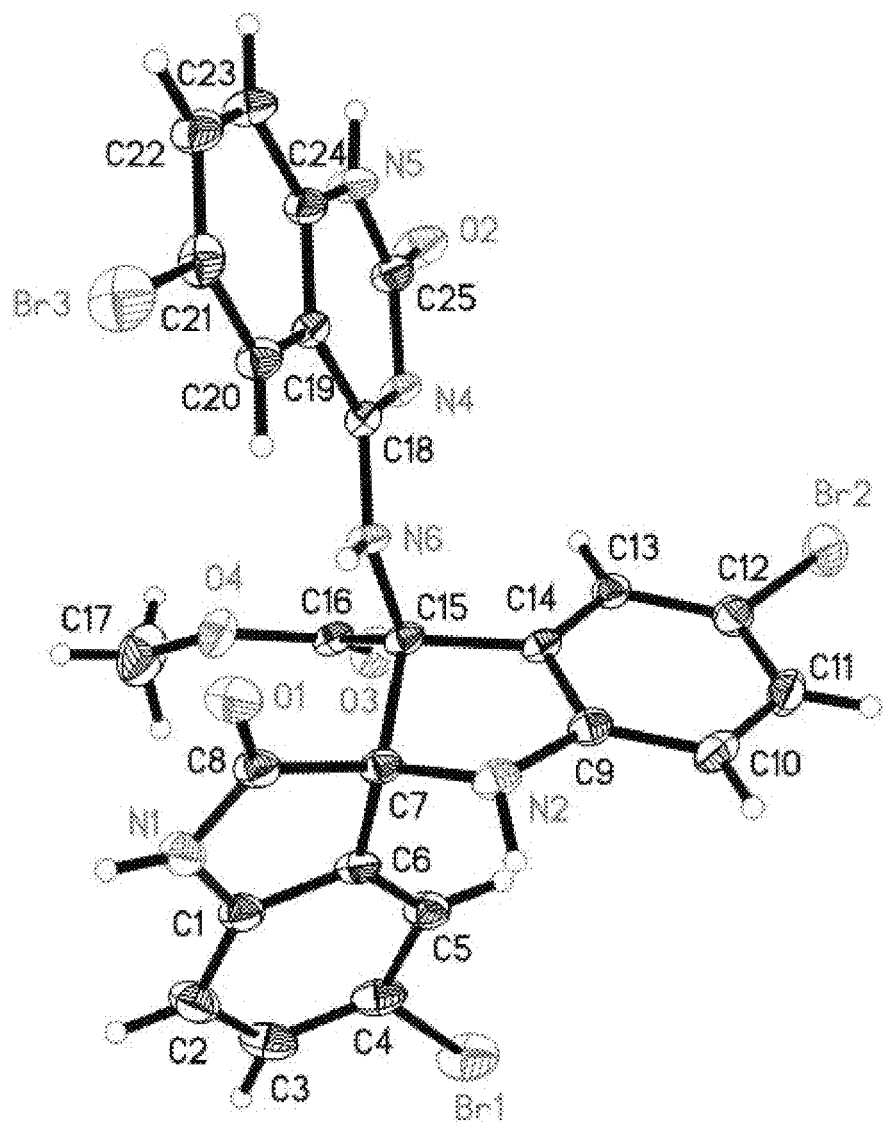

PREPARATION AND APPLICATION OF A 5-BROMOQUINAZOLINE DERIVATIVE

TECHNICAL FIELD

The invention relates to a new chemical compound and application thereof, in particular to a preparation method of a quinazoline, definitely preparation and application of a 5-bromoquinazoline derivative.

BACKGROUND ART

The 5-bromoquinazoline derivative is a heterocyclic compound. The synthesis method of compound thereof has been reported in similar literature. [1] Because it is a Lewis base, the application thereof can be developed as an organic catalyst and anti-cancer reagent:

REFERENCES

1. Synthesis and pharmacological properties of 4-phenylquinazolin-2-ones, Voronina, T. A.; Gordiichuk, G. N.; Andronati, S. A.; Garibova, T. L.; Zhilina, Z. I. Khimiko-Farmatsevticheskii Zhurnal (1981), 15(7), 55-7.

SUMMARY OF THE INVENTION

The invention aims to provide a quinazoline derivative and a preparation method thereof, and the technical problem to be solved is to synthesize the target product in one step.

The quinazoline and preparation method thereof referred to in the invention are compounds represented by the following chemical formula prepared from 5-bromoisatin and ammonium formate in absolute methanol solution:

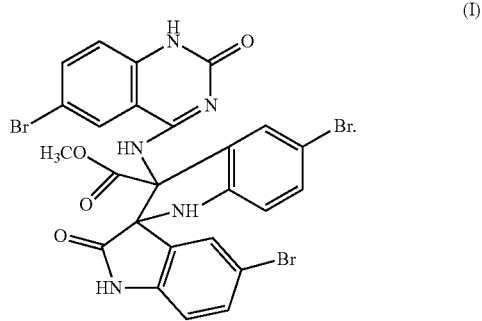 [SMILES: COC(=O)C1(Nc2nc(=O)[nH]c3ccc(Br)cc23)c2cc(Br)ccc2NC12C(=O)Nc1ccc(Br)cc12]

(I)

Chemical name: 3-[5, 5'-dibromo-3-((6-bromo-2-oxo-1, 2-dihydroquinazoline-4-amino)-2'-oxo (2,3'-spirobisindole)] methyl formate, be called compound (I) for short. The compound has a good catalytic effect in nitrile silicification reaction of benzaldehyde and auto-polymerization reaction of benzophenone hydrazone, the conversion rates thereof respectively reach 39% and 76%, also and the can be used as an anti-cancer reagent which has certain anti-cancer activity of breast cancer, liver cancer and lung cancer.

The synthesis method comprises synthesis and separation, the synthesis comprises weighing 1.18 g of 5-bromoisatin, 2.5503 g of ammonium formate and 100 ml of absolute methanol in a 250 mL round-bottom flask, heating, stirring and refluxing for 48 h, stopping reaction, rotating to obtain 1.6033 g of filter residue crude product, carrying out column chromatography separation by using dichloromethane and absolute methanol according to a volume ratio of 1:1, and obtaining a target crystal compound I.

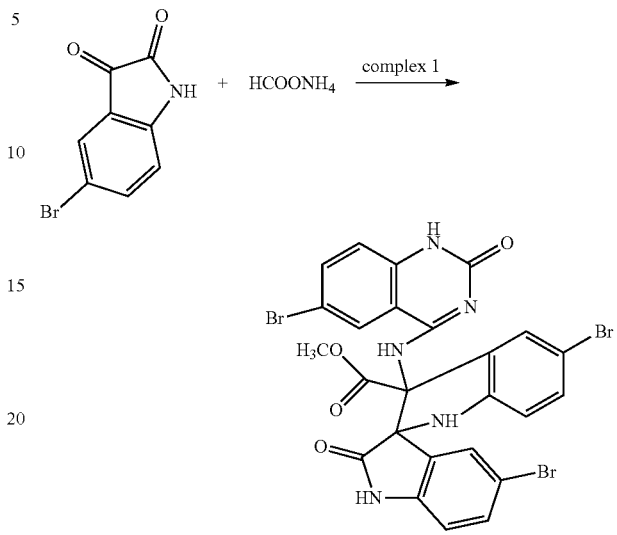

The synthesis method in the invention can obtain the target product in one step, has simple process and convenient operation.

The reaction mechanism of the reaction is complicated, 6-bromoisatin and ammonium formate react with 1 mol % palladium complex in methanol solution, and the carbonyl group reacts with ammonium formate to convert to amino group. After condensation and reaction of methanol, compound I is obtained in one step.

DESCRIPTION OF ACCOMPANYING DRAWINGS

FIG. 1 is the X-ray diffraction analysis of compound I.

SPECIFIC EMBODIMENTS OF THE INVENTION

1. Preparation of Chiral Palladium Complexes (1) Preparation of [1,4-(4R)-diisopropyl-2-oxazolinyl] benzene In a 100 mL two-neck flask, under conditions which exclude water and oxygen, add 1.4054 g of anhydrous $ZnCl_2$ (10.64 mmol), 40 ml of chlorobenzene, 5.0236 g of 1,4-dicyanobenzene (39.2 mmol), 16.2075 g of L-Valinol, the mixture was refluxed at high temperature for 60 h, stopping the reaction, the solvent was removed under reduced pressure, the residue was dissolved in water, and extracted with $CHCl_3$ (20 mL×2), the organic phase was dried with anhydrous sodium sulfate, the solvent was removed by rotating, and column chromatography was carried out on the crude product by using petroleum ether/dichloromethane (4:1), a light green viscous liquid was obtained, yield 52%; white crystals, fusion point: 48-50° C., [a]5D=+111.9° (c=0.429, CHCl3); 1HNMR (500 MHz, CDCl3, 27° C.), δ (ppm)=7.97 (s, 4H), 4.39~4.43 (t, 3.18 Hz, 1H), 4.09~4.15 (m, 2H), 1.85~1.86 (m, 1H), (d, J=6.24 Hz, 6H), 0.86~0.96 (d, J=6.24 Hz, 6H). 13CNMR 18.13, 19.03, 32.85, 70.26, 72.76, 128.10, 128.16, 130.32, 162.82.IR: 3273, 2976, 2960, 2932, 2889, 2869, 1643, 1512, 1469, 1408, 1382, 1366, 1350, 1320, 1296, 1276, 1214, 1180, 1108, 1077, 1047, 1014, 971, 955, 900, 891, 838, 726, 698, 675, 659, 540.HRMS (EI): m/z (%): calcd for C18H24N2O2: 300.1838; found: 300.1833.

(2) Preparation of Complex of Bis{[1,4-(4S)-diisopropyl-2-oxazoline benzene] palladium chloride}

In a 100 mL two-neck flask, under conditions which exclude water and oxygen, add 1.5603 g of palladium chloride (4.92 mmol), 1.0435 g of 1,4-(4R)-diisopropyl-2-oxazoline benzene (3.48 mmol), 30 ml of chlorobenzene, the mixture was refluxed at high temperature for 48 h, stopping the reaction, the solvent was removed under reduced pressure, the residue was dissolved in chloroform and ethanol, and naturally volatilized to obtain a red-brown complex to obtain crystals, yield 92%; m.p.: >200° C., [a]5D=+512.8° (c 0.0564, CH3OH); 1H NMR (600 MHz, CDCl3), δ' ppm 8.81 (s, 8H, ArH), 4.61-4.63 (m, 4H, CH×4), 4.53 (t, J=9.6 Hz, 4H, CH×4), 4.44 (t, J=8.5 Hz, 4H, CH×4), 3.07-3.10 (m, 4H), 1.18 and 1.15 (dd, J=6.7, 7.2 Hz, 24H, CH3×4); 13C NMR (150 MHz, CDCl$_3$) ppm 166.8, 130.1 (×2), 129.3, 72.0, 69.1, 30.7, 19.0, 15.6; vmax (cm-1) 3487, 3049, 2957, 2929, 2872, 1642, 1609, 1572, 1509, 1480, 1464, 1416, 1379, 1331, 1288, 1246, 1178, 1141, 1123, 1099, 1045, 1018, 959, 933, 899, 854, 804, 770, 722, 693, 438; elemental analysis C36H48N4Cl4O4Pd2, test value C, 45.26%, H, 5.06%, N, 5.86%; theoretical value: C, 45.32%, H, 5.24%, N, 5.48%;

2. Preparation of Complex I weighing 1.18 g of 5-bromoisatin, 2.5503 g of ammonium formate and 100 ml of absolute methanol in a 250 mL round-bottom flask, heating, stirring and refluxing for 48 h, stopping reaction, rotating to obtain 1.6033 g of filter residue crude product, carrying out column chromatography (petroleum ether/dichloromethane, 1/1) separation, and obtaining 0.8365 g of crystal compound, yield: 23.2%; fusion point: >250° C.; elemental analysis data: theoretical value: C: 43.51%; H: 2.34%; N: 10.15%; measured value: C: 43.69%; H: 2.65%; N: 9.98%; ERMS (C25H16Br3N5O4, m/e): theoretical value: 686.8752; measured value: 686.8969; 1H NMR (600 MHz, CDCl3), δ ppm 11.40 (s, 1H), 11.08 (s, 1H), 9.59 (s, 1H), 8.15 (s, 1H), 8.07 (d, J=2.1 Hz, 1H), 7.76 (d, J=1.9 Hz, 1H), 7.68, 7.66 (dd, J=1.9 Hz, 1.8 Hz, 1H), 7.44, 7.43 (dd, J=2.0 Hz, 2.0 Hz, 1H), 7.30, 7.28 (dd, J=2.1 Hz, 2.1 Hz, 1H), 7.15 (d, J=8.7 Hz, 1H), 6.88-6.92 (m, 2H), 6.71 (d, J=8.4 Hz, 1H), 3.23 (s, 3H); 13C NMR (150 Mhz, CDCl3) ppm 176.1, 166.9, 157.1, 154.5, 149.6, 141.7, 140.4, 136.5, 132.8, 132.3, 131.7, 129.9, 128.2, 126.9, 124.6, 117.7, 113.7, 113.0, 112.5, 111.8, 109.7, 109.4, 71.5, 71.2, 52.2; IR Spectroscopy data: (KBr; v, cm-1): 3423, 2924, 1698, 1636, 1438, 1384, 1337, 1164, 1111, 1061, 899, 823, 785; Crystal data of compounds:

| | |
|---|---|
| empirical formula | C25H16Br3N5O4 |
| molecular weight | 690.16 |
| temperature | 293.4(2) K |
| wave length | 0.71073 A |
| crystal system, space groups | triclinic system, P −1 |
| cell parameters | a = 8.7881(5) Å alpha = 98.254(2) deg. |
| | b = 9.9375(5) Å beta = 97.014(2) deg. |
| | c = 17.8389(9) Å gamma = 112.154 deg. |
| volume | 1401.29 (13) Å^3 |
| electric density | 2, 1.636Mg/m^3 |
| absorption/correction parameter | 4.357 mm^ − 1 |
| number of electrons in a cell | 676 |
| crystal size | 0.15 × 0.12 × 0.1 mm |
| range of angle (Theta) | 2.351 to 27.540 |
| collection range of HKL indicators | −10 <= h < 11, −12 <= k < 12, −23 <= l <= 23 |
| collect/independent diffraction data | 23227/6418 [r(int) = 0.0400] |
| data integrity when theta = 30.5 | 99.8% |
| absorption/correction method | milt-slice scan |
| maximum/minimum transmittance | 0.7456 and 0.5613 |
| refinement method | F^2 matrix least square method |
| data number/restrict number of use/parameter number | 6418/0/339 |
| refinement method | 0.982 |
| consistency factor of the diffraction point | R1 = 0.0432, wR2 = 0.1357 |
| anastomosis factor of diffraction can be observed | R1 = 0.0702, wR2 = 0.1534 |
| maximum peak and peak valley on the difference Fourier diagram | 0.516 and −0.570e · A^ − 3 |

| Typical bond length data for crystals: | |
|---|---|
| Br(1)—C(4) | 1.901(4) |
| Br(2)—C(12) | 1.896(4) |
| Br(3)—C(21) | 1.891(4) |
| O(1)—C(8) | 1.226(4) |
| O(2)—C(25) | 1.245(4) |
| O(3)—C(16) | 1.194(4) |
| O(4)—C(16) | 1.328(4) |
| O(4)—C(17) | 1.459(5) |
| N(1)—H(1) | 0.8600 |
| N(1)—C(1) | 1.402(5) |
| N(1)—C(8) | 1.334(5) |
| N(2)—C(7) | 1.473(5) |
| N(2)—C(9) | 1.398(5) |
| N(2)—H(2) | 0.89(5) |
| N(6)—H(6) | 0.8600 |
| N(6)—C(15) | 1.454(4) |
| N(6)—C(18) | 1.338(4) |
| N(4)—C(18) | 1.319(4) |
| N(4)—C(25) | 1.364(4) |
| N(5)—H(5) | 0.8600 |
| N(5)—C(24) | 1.375(5) |
| N(5)—C(25) | 1.366(5) |
| C(1)—C(2) | 1.390(5) |
| C(1)—C(6) | 1.377(5) |
| C(2)—H(2A) | 0.9300 |

| | |
|---|---|
| C(2)—C(3) | 1.384(6) |
| C(3)—H(3) | 0.9300 |
| C(3)—C(4) | 1.376(6) |
| C(4)—C(5) | 1.379(5) |
| C(5)—H(5A) | 0.9300 |
| C(5)—C(6) | 1.385(5) |
| C(6)—C(7) | 1.516(5) |
| C(7)—C(8) | 1.554(5) |
| C(7)—C(15) | 1.593(4) |
| C(9)—C(10) | 1.379(5) |
| C(9)—C(14) | 1.390(5) |
| C(10)—H(10) | 0.9300 |
| C(10)—C(11) | 1.394(6) |
| C(11)—H(11) | 0.9300 |
| C(11)—C(12) | 1.381(6) |
| C(12)—C(13) | 1.395(5) |
| C(13)—H(13) | 0.9300 |
| C(13)—C(14) | 1.374(4) |
| C(14)—C(15) | 1.532(4) |
| C(15)—C(16) | 1.524(5) |
| C(17)—H(17A) | 0.9600 |
| C(17)—H(17B) | 0.9600 |
| C(17)—H(17C) | 0.9600 |
| C(18)—C(19) | 1.454(5) |
| C(19)—C(20) | 1.408(5) |
| C(19)—C(24) | 1.382(5) |
| C(20)—H(20) | 0.9300 |
| C(20)—C(21) | 1.374(5) |
| C(21)—C(22) | 1.385(6) |
| C(22)—H(22) | 0.9300 |
| C(22)—C(23) | 1.380(6) |
| C(23)—H(23) | 0.9300 |
| C(23)—C(24) | 1.395(5) |

| bond angle data of crystals C(16)—O(4)—C(17) | |
|---|---|
| C(1)—N(1)—H(1) | 124.1 |
| C(8)—N(1)—H(1) | 124.1 |
| C(8)—N(1)—C(1) | 111.8(3) |
| C(7)—N(2)—H(2) | 118(3) |
| C(9)—N(2)—C(7) | 106.1(3) |
| C(9)—N(2)—H(2) | 110(3) |
| C(15)—N(6)—H(6) | 116.8 |
| C(18)—N(6)—H(6) | 116.8 |
| C(18)—N(6)—C(15) | 126.4(3) |
| C(18)—N(4)—C(25) | 119.3(3) |
| C(24)—N(5)—H(5) | 118.2 |
| C(25)—N(5)—H(5) | 118.2 |
| C(25)—N(5)—C(24) | 123.6(3) |
| C(2)—C(1)—N(1) | 127.6(4) |
| C(6)—C(1)—N(1) | 110.5(3) |
| C(6)—C(1)—C(2) | 121.9(4) |
| C(1)—C(2)—H(2A) | 121.5 |
| C(3)—C(2)—C(1) | 116.9(4) |
| C(3)—C(2)—H(2A) | 121.5 |
| C(2)—C(3)—H(3) | 119.5 |
| C(4)—C(3)—C(2) | 120.9(4) |
| C(4)—C(3)—H(3) | 119.5 |
| C(3)—C(4)—Br(1) | 118.8(3) |
| C(3)—C(4)—C(5) | 122.2(4) |
| C(5)—C(4)—Br(1) | 119.0(3) |
| C(4)—C(5)—H(5A) | 121.4 |
| C(4)—C(5)—C(6) | 117.2(4) |
| C(6)—C(5)—H(5A) | 121.4 |
| C(1)—C(6)—C(5) | 120.9(3) |
| C(1)—C(6)—C(7) | 107.9(3) |
| C(5)—C(6)—C(7) | 131.2(3) |
| N(2)—C(7)—C(6) | 115.5(3) |
| N(2)—C(7)—C(8) | 113.0(3) |
| N(2)—C(7)—C(15) | 101.4(3) |
| C(6)—C(7)—C(8) | 101.7(3) |
| C(6)—C(7)—C(15) | 112.5(3) |
| C(8)—C(7)—C(15) | 113.3(3) |
| O(1)—C(8)—N(1) | 127.1(3) |
| O(1)—C(8)—C(7) | 124.9(3) |
| N(1)—C(8)—C(7) | 107.9(3) |
| C(10)—C(9)—N(2) | 127.2(3) |
| C(10)—C(9)—C(14) | 121.0(3) |
| C(14)—C(9)—N(2) | 111.8(3) |
| C(9)—C(10)—H(10) | 121.3 |
| C(9)—C(10)—C(11) | 117.4(3) |
| C(11)—C(10)—H(10) | 121.3 |
| C(10)—C(11)—H(11) | 119.6 |
| C(12)—C(11)—C(10) | 120.7(4) |
| C(12)—C(11)—H(11) | 119.6 |
| C(11)—C(12)—Br(2) | 119.1(3) |
| C(11)—C(12)—C(13) | 122.2(3) |
| C(13)—C(12)—Br(2) | 118.6(3) |
| C(12)—C(13)—H(13) | 121.9 |
| C(14)—C(13)—C(12) | 116.2(3) |
| C(14)—C(13)—H(13) | 121.9 |
| C(9)—C(14)—C(15) | 107.4(3) |
| C(13)—C(14)—C(9) | 122.4(3) |
| C(13)—C(14)—C(15) | 130.2(3) |
| N(6)—C(15)—C(7) | 107.2(2) |
| N(6)—C(15)—C(14) | 112.1(3) |
| N(6)—C(15)—C(16) | 113.0(3) |
| C(14)—C(15)—C(7) | 99.6(2) |
| C(16)—C(15)—C(7) | 108.9(3) |
| C(16)—C(15)—C(14) | 115.0(3) |
| O(3)—C(16)—O(4) | 125.3(3) |
| O(3)—C(16)—C(15) | 125.3(3) |
| O(4)—C(16)—C(15) | 109.1(3) |
| O(4)—C(17)—H(17A) | 109.5 |
| O(4)—C(17)—H(17B) | 109.5 |
| O(4)—C(17)—H(17C) | 109.5 |
| H(17A)—C(17)—H(17B) | 109.5 |
| H(17A)—C(17)—H(17C) | 109.5 |
| H(17B)—C(17)—H(17C) | 109.5 |
| N(6)—C(18)—C(19) | 117.9(3) |
| N(4)—C(18)—N(6) | 118.9(3) |
| N(4)—C(18)—C(19) | 123.2(3) |
| C(20)—C(19)—C(18) | 124.4(3) |
| C(24)—C(19)—C(18) | 116.5(3) |
| C(24)—C(19)—C(20) | 119.0(3) |
| C(19)—C(20)—H(20) | 120.2 |
| C(21)—C(20)—C(19) | 119.6(3) |
| C(21)—C(20)—H(20) | 120.2 |
| C(20)—C(21)—Br(3) | 119.9(3) |
| C(20)—C(21)—C(22) | 121.0(4) |
| C(22)—C(21)—Br(3) | 119.1(3) |
| C(21)—C(22)—H(22) | 120.0 |
| C(23)—C(22)—C(21) | 119.9(4) |
| C(23)—C(22)—H(22) | 120.0 |
| C(22)—C(23)—H(23) | 120.2 |
| C(22)—C(23)—C(24) | 119.5(3) |
| C(24)—C(23)—H(23) | 120.2 |
| N(5)—C(24)—C(19) | 118.0(3) |
| N(5)—C(24)—C(23) | 121.1(3) |
| C(19)—C(24)—C(23) | 120.9(3) |
| O(2)—C(25)—N(4) | 121.6(3) |
| O(2)—C(25)—N(5) | 119.2(3) |
| N(4)—C(25)—N(5) | 119.2(3). |

3. Application of Nitrile Silicification Reaction 0.01 g compound I, 0.1 mL of benzaldehyde, 0.3 ml of TMSCN, 1 mL of THF solution, successively added at 20~30° C., 3 days later, quenched by adding water, after passing through the column (petroleum ether/dichloromethane: 5/1), a colorless oily liquid, conversion rate: 39%; $^1$H NMR (300 MHz, CDCl$_3$) 7.56-7.59 (m, 0.9 Hz, 2H), 7.31-7.34 (m, 3H), 5.43 (s, 1H), 0.16 (s, 9H). $^{13}$C NMR (75 MHz, CDCl$_3$) 136.1, 128.8 (×2), 126.2 (×2), 119.1, 63.5, −0.39 (×3)

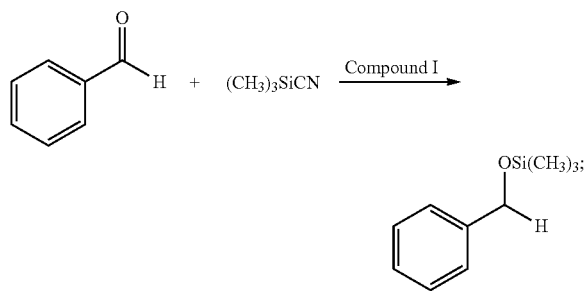

4. Application of Polymerization Reaction of Benzophenone Hydrazone

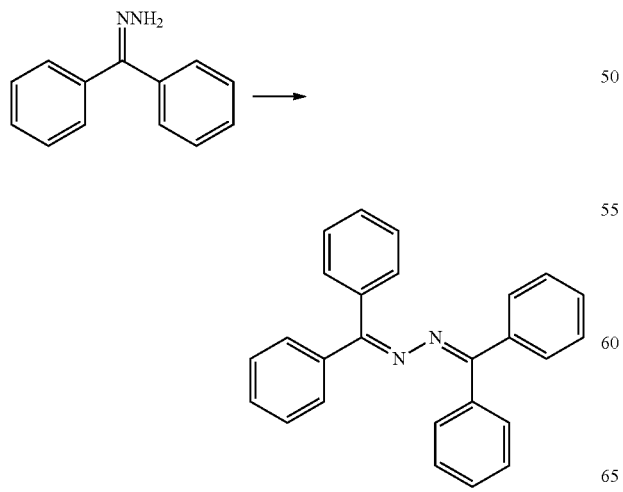

Weighing 0.2 g of benzophenone hydrazone and 0.069 g compound I in a 25 mL round-bottom flask, adding 2.0 mL of anhydrous methanol as a solvent to the above flask, stirring to dissolve, heating and refluxing for 48 h, stopping reaction, and detecting with 1HNMR. The conversion rate thereof is: 76%; 1 H NMR (400 MHz, CDCl3) δ 7.50-7.44 (m, 4H), 7.43-7.36 (m, 6H), 7.36-7.25 (m, 10H).

5. Application of Anti-Cancer Activity

The compound (I) designed and synthesized according to the objective of the invention has been shown strong inhibitory activity (ED50<10.0 µg/mL) in tests of a variety of cancer cells such as leukemia (HL-60), liver cancer (SMMC-7721), colon cancer (SW480), and breast cancer cells (MCF-7). Therefore, it is expected that the compounds of the invention can be used to treat a variety of cancers, such as lung cancer, breast cancer, and breast cancer cells. The test results of some anti-cancer activities of the compounds of the invention are shown in Table 1:

TABLE 1

Anti-cancer activity data (IC50 value) of quinazoline derivative (I)

| | cell line | | | | | | | |
|---|---|---|---|---|---|---|---|---|
| | leukemia HL-60 | | hepatoma carcinoma cell SMMC-7721 | | colon cancer SW480 | | breast cancer cell MCF-7 | |
| sample | average value | standard deviation | average value | standard deviation | average value | standard deviation | average value | standard deviation |
| quinazoline derivative (I) | 17.35 | ±0.17 | 31.43 | ±0.78 | 36.06 | ±0.15 | 20.02 | ±0.52 |

The invention claimed is:

1. A 5-bromoquinazoline derivative (I), structural formula thereof is as follows:

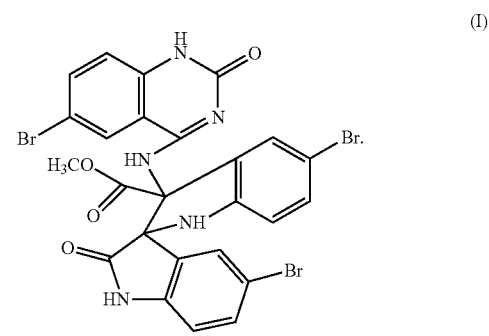 [SMILES: COC(=O)C1(Nc2nc(=O)[nH]c3ccc(Br)cc23)c2cc(Br)ccc2NC12C(=O)Nc1ccc(Br)cc12]

2. The 5-bromoquinazoline derivative crystal (I) of claim 1, at the temperature of 293(2) K, and on the Oxford X-ray single crystal diffractometer, diffraction data is collected by w-O scanning mode with MoKα rays (λ=0.71073 Å) monochromatized by a graphite monochromator, wherein the crystal belongs to the triclinic system, P-1, cell parameters:

a=8.7881(5) Å alpha=98.254(2)deg; b=9.9375(5) Å beta=97.014(2)deg; c=17.8389(9) Å gamma=112.154deg.

3. A synthesis method of the 5-bromoquinazoline derivative compound (I) of claim 1, comprising heating 5-bromoisatin and ammonium formate in absolute methanol to obtain the final product.

4. A method of synthesizing benzyloxy-trimethylsilane, comprising reacting benzaldehyde and TMSCN with a catalyst of formula (I) according to claim 1 in THF at room temperature to obtain the product.

5. A method of synthesizing 1,2-bis(diphenylmethylene) hydrazine, comprising heating a reaction of benzophenone hydrazone with a catalyst of formula (I) according to claim 1 in methanol to obtain the product.

* * * * *